(12) United States Patent
Brueggemeier et al.

(10) Patent No.: US 7,572,919 B2
(45) Date of Patent: Aug. 11, 2009

(54) HETEROARYL-CONTAINING ISOFLAVONES AS AROMATASE INHIBITORS

(75) Inventors: Robert W. Brueggemeier, Dublin, OH (US); Young-Woo Kim, Columbus, OH (US); John C. Hackett, Dublin, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 78 days.

(21) Appl. No.: 11/212,229

(22) Filed: Aug. 26, 2005

(65) Prior Publication Data

US 2006/0183923 A1 Aug. 17, 2006

Related U.S. Application Data

(60) Provisional application No. 60/604,667, filed on Aug. 26, 2004.

(51) Int. Cl.
*C07D 311/04* (2006.01)
*C07D 311/74* (2006.01)
*C07D 401/02* (2006.01)

(52) U.S. Cl. ............... 546/283.1; 549/400; 549/401

(58) Field of Classification Search ............... None
See application file for complete search history.

(56) References Cited

U.S. PATENT DOCUMENTS

2004/0087586 A1 5/2004 Brueggemeier et al.

OTHER PUBLICATIONS

International Search Report and Written Opinion from PCT/US05/30401, mailed Aug. 8, 2007.
Kim, Young-Woo, "Novel 2-Substituted Isoflavones: A Privileged Structure Approach to New Agents for Hormone-Dependent Breast Cancer," PhD Dissertation, Aug. 2003, The Ohio State University, Columbus, OH.
Kim, Young-Woo et al., "Synthesis and Aromatase Ihibitory Activity of Novel Pyridine-Containing Isoflavones," J. Med. Chem., Jul. 2, 2004, vol. 47, pp. 4032-4040, The Ohio State University, Columbus, OH.

*Primary Examiner*—Zinna N Davis
(74) *Attorney, Agent, or Firm*—Calfee, Halter & Griswold, LLP (57) ABSTRACT

Compounds and methods useful for treating and prevention of cancer, particularly hormone-dependent breast cancer. Provided are compounds of formula I:

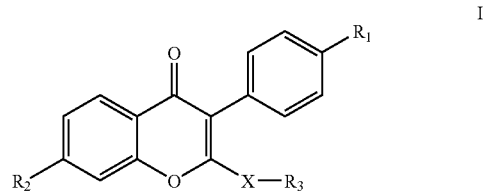

wherein X is selected from O, N, S, SO, $SO_2$, and $S(CH_2)_n$, wherein n=1-10; $R_1$ and $R_2$ may be the same or different and are selected from H, OH, $OCH_3$, $OCH_2CH_3$, $OCH_2C_6H_5$, $NH_2$, $NHCH_3$, $N(CH_3)_2$, $CH_3$, $CH_2CH_3$, $CH_2CH_2CH_3$, $CH(CH_3)_2$, $C(CH_3)_3$, $NO_2$, F, Cl, Br, $CF_3$, SH, $SCH_3$, $SCH_2CH_3$, $OCOCH_3$, $OCOC(CH_3)_3$, $OCOCH_2COOH$, and CN; and $R_3$ is a nitrogen-containing heterocyclic ring. Also provided are method for treating or preventing cancer in a subject by administering a therapeutically effective amount of a heteroaryl-containing isoflavone, or a pharmaceutically acceptable salt or prodrug thereof, to a subject in need of treatment. Also provided is a method for the synthesis of 2-substituted isoflavones by first reacting deoxybenzoins with a phase transfer catalyst to provide a 2-(alkylthio)isoflavone; second deprotecting the 2-(alkylthio)isoflavone; and third applying selective debenzylation to form the final compound.

10 Claims, 2 Drawing Sheets

Fig. 1

$R_1$ = H, Me, OMe, OH
$R_2$ = OH, OMe, OBn
$R_3$ = allyl, benzyl, pyridylmethyl

Scheme 1. Synthesis of isoflavones 3a–k.

Scheme 2. Synthesis of isoflavones 4a–g.

HETEROARYL-CONTAINING ISOFLAVONES AS AROMATASE INHIBITORS

CROSS-REFERENCE TO RELATED APPLICATIONS

This application claims priority to U.S. Provisional Patent Application No. 60/604,667, titled "HETEROARYL-CONTAINING ISOFLAVONES AS AROMATASE INHIBITORS" filed Aug. 26, 2004, the entirety of which is incorporated herein by reference.

STATEMENT REGARDING FEDERALLY SPONSORED RESEARCH

This invention was supported at least in part by US Army Medical Research and Material Command Grants DAMD 17-99-1-9342 and DMAD 17-00-1-0388. The Federal Government may have certain rights in this invention.

BACKGROUND OF THE INVENTION

Flavonoids are a diverse group of plant-derived chemicals that are produced by various higher plants, which can be found in numerous food sources such as fruits, vegetables, legumes, and whole grains. Compounds in this class have shown a wide variety of biological activities such as anti-inflammatory, antibacterial, antifungal and anticancer activities. In particular, due to their structural and functional similarities to endogenous estrogens, flavonoids have attracted considerable interest as alternative estrogens, termed phytoestrogens, and extensively studied for their potential role in many estrogen-dependent diseases including breast cancer. In fact, numerous flavonoids have shown interesting pharmacological activities and inhibitory activities against aromatase enzyme.

Genistein (GEN) is the most abundant isoflavone in soybeans. Some researchers suggest that GEN may be responsible for the relatively low incidence of hormone-dependent breast cancer in certain regions with high consumption of soy foods. Indeed, GEN has been one of the most widely studied natural products and has shown a number of important biological activities in breast cancer biology. GEN displays moderate binding to estrogen receptors, as well as exhibiting antiproliferative activity in many can cell lines mediated by several mechanisms of action. Furthermore, it is known that GEN exerts many beneficial effects on endogenous estrogens on several tissues such as bone and cardiovascular system. In addition to estrogenic activities, GEN has also demonstrated a variety of other interesting biological activities. It exerts antioxidant activity and is a potent scavenger of hydrogen peroxide. In addition, GEN has shown inhibitory abilities against various enzymes involved in tumor development and growth such as protein tyrosine kinases, DNA topoisomerases, and protein kinase C (PKC). It has also shown to inhibit angiogenesis and induce apoptosis and cell cycle arrest in the G2-phase. While GEN is the most extensively studied flavonoid for its versatile biological activities, it has been reported to exert no or very weak aromatase inhibition.

Aromatase has been a particularly attractive target for inhibition in the treatment of hormone-dependent breast cancer since the aromatization is the last step in steroid biosynthesis and is the rate-limiting step for estrogen synthesis. In general, however, isoflavones are considered less effective than flavones or flavonones in terms of aromatase inhibition. For this reason, to the best of our knowledge, there has been no medicinal chemistry effort to develop isoflavones-based aromatase inhibitors.

SUMMARY OF THE INVENTION

In one aspect, provided herein are compounds for treating or preventing cancer, particularly breast cancer in a subject. The compounds are new heteroaryl-containing isoflavones and pharmaceutical compositions that contain one of more of the heteroaryl-containing isoflavones as described herein and derivatives thereof. It is preferred that the compounds described herein are aromatase inhibitors. The heteroaryl-containing isoflavones have the following base structure:

wherein

X is selected from the group consisting of O, N, S, $S(CH_2)_n$, wherein n=1-10; SO, and $SO_2$; and preferably, X is S or $S(CH_2)_n$, wherein n=1, 2, 3, and so forth;

$R_1$ and $R_2$ can be the same or different and are selected from the group consisting of H, OH, $OCH_3$, $OCH_2CH_3$, $OCH_2C_6H_5$, $NH_2$, $NHCH_3$, $N(CH_3)_2$, $CH_3$, $CH_2CH_3$, $CH_2CH_2CH_3$, $CH(CH_3)_2$, $C(CH_3)_3$, $NO_2$, F, Cl, Br, $CF_3$, SH, $SCH_3$, $SCH_2CH_3$, $OCOCH_3$, $OCOC(CH_3)_3$, $OCOCH_2COOH$, and CN; and

$R_3$ comprises a nitrogen-containing heterocyclic moiety. Preferably, $R_3$ is a 5- or 6-membered ring containing 1-3 nitrogen atoms in the ring, though other sized rings and other numbers of nitrogen atoms in the ring may be used. The ring may be selected from, but is not limited to, the group consisting of imidazole, triazole, pyrimidine, and pyridine. The nitrogen-containing heterocyclic moiety may contain substituents on the heterocyclic ring. Those substituents may be selected from the group consisting of H, OH, $OCH_3$, $OCH_2CH_3$, $NH_2$, $NHCH_3$, $N(CH_3)_2$, $NO_2$, $CH_3$, $CH_2CH_3$, $CH_2CH_2CH_3$, $CH(CH_3)_2$, $C(CH_3)_3$, F, Cl, Br, $CF_3$, SH, $SCH_3$, $SCH_2CH_3$, CN and combinations thereof.

Some preferred compounds described herein include the following structures wherein $R_1$ and $R_2$ are as described above and $R_3$ is selected from the following:

wherein X and $R_1$, $R_2$, and $R_3$ are as described above, and wherein X—$R_3$ is selected from:

wherein n = 0, 1, 2...
wherein R₄ = H, CH₃, CH₂CH₃, NH₂...

Also provided is a method of using the compounds described herein in the treatment of cancer. In one embodiment, the method is a method for the treatment of breast cancer, particularly, but not limited to hormone-dependent breast cancer. The method comprises administering a therapeutically effective amount of a heteroaryl-containing isoflavone of the present invention, or a derivative or pharmaceutically acceptable salt or ester thereof, to a subject in need of treatment. The heteroaryl-containing isoflavone compound can be administered in accordance with conventional methods, and in doses similar to drugs currently available for the treatment of breast cancer. The heteroaryl-containing isoflavone compounds of present invention may also be used as part of a combination therapy. Also provided is a method for the prevention of breast cancer in subjects who are susceptible to developing breast cancer, comprising administering a therapeutically effective amount of a compound of a compound of the present invention, or a derivative or pharmaceutically acceptable salt or ester thereof.

Further provided is a method for the preparation of 2-substituted isoflavones, the method comprising the steps of a) reacting deoxybenzoins with a phase transfer catalyst to provide a 2-(alkylthio)isoflavone; b) deprotecting the 2-(alkylthio)isoflavone; and c) applying selective debenzylation to form the final compound.

DETAILED DESCRIPTION OF THE INVENTION

The role of endogenous estrogens in the development of hormone-dependent breast cancer has been widely recognized, and inhibition of the biosynthesis of estrogens has been on the most promising and logical therapeutic strategies for the disease. Among a number of enzymes involved in estrogen biosynthesis, aromatase is a particularly attractive target for inhibition because aromatization is the final, rate-limiting step in estrogen biosynthesis; therefore, its blockade should not interfere with the production of other steroids. Aromatase inhibitors are typically classified by the chemical structures, namely, steroidal aromatase inhibitors and non-steroidal aromatase inhibitors. The nonsteroidal compounds are reversible inhibitors that compete with the natural substrates, androstenedione and testosterone, for binding to the active site of aromatase.

The present invention provides both new heteroaryl-containing isoflavone compounds and methods of using those compounds. The compounds of the present invention encompass 2-(4-pyridylmethyl)thioisoflavones, as well as salts, esters, and derivatives and related compounds. The present invention further encompasses derivatives of these compounds as well as pharmaceutical compositions that contain one of more of the heteroaryl-containing isoflavones of the present invention. The heteroaryl-containing isoflavones have the following structure:

wherein

X is selected from the group consisting of O, N, S, and $S(CH_2)_n$, wherein n=1-10; SO, and $SO_2$; and preferably, X is S, $S(CH_2)_n$, wherein n=1, 2, 3, and so forth;

$R_1$ and $R_2$ can be the same or different and are selected from the group consisting of H, OH, $OCH_3$, $OCH_2CH_3$, $OCH_2C_6H_5$, $NH_2$, $NHCH_3$, $N(CH_3)_2$, $CH_3$, $CH_2CH_3$, $CH_2CH_2CH_3$, $CH(CH_3)_2$, $C(CH_3)_3$, $NO_2$, F, Cl, Br, $CF_3$, SH, $SCH_3$, $SCH_2CH_3$, $OCOCH_3$, $OCOC(CH_3)_3$, $OCOCH_2COOH$, and CN;

$R_3$ comprises a nitrogen-containing heterocyclic moiety. Preferably, $R_3$ is a 5- or 6-membered ring containing 1-3 nitrogen atoms in the ring, though other sized rings and other numbers of nitrogen atoms in the ring may be used. The ring may be selected from, but is not limited to, the group consisting of imidazole, triazole, pyrimidine, and pyridine. The nitrogen-containing heterocyclic moiety may contain substituents on the heterocyclic ring. Those substituents may be selected from the group consisting of H, OH, $OCH_3$, $OCH_2CH_3$, $NH_2$, $NHCH_3$, $N(CH_3)_2$, $NO_2$, $CH_3$, $CH_2CH_3$, $CH_2CH_2CH_3$, $CH(CH_3)_2$, $C(CH_3)_3$, F, Cl, Br, $CF_3$, SH, $SCH_3$, $SCH_2CH_3$, CN and combinations thereof.

While the compounds of the present invention may work through any mechanism, it is preferred, though not required, that the compounds have aromatase inhibitory activity.

Some preferred compounds of the present invention include the following wherein $R_1$ and $R_2$ are as described above and $R_3$ is selected from the following:

wherein X and $R_1$, $R_2$, and $R_3$ are as described above, and wherein X—$R_3$ is selected from:

wherein n = 0, 1, 2...
wherein $R_4$ = H, $CH_3$, $CH_2CH_3$, $NH_2$...

By "treating" is meant curing, ameliorating or tempering the severity of the cancer or the symptoms associated therewith. The terms "treating," "treatment," and "therapy" as used herein refer to curative therapy, prophylactic therapy, and preventative therapy.

"Preventing" or "prevention" means preventing the occurrence of the cancer, or tempering the severity of the cancer if it is develops subsequent to the administration of the instant compositions. This preventing the onset of a clinically evident unwanted cell proliferation altogether or preventing the onset of a preclinically evident stage of unwanted rapid cell proliferation in individuals at risk. Also intended to be encompassed by this definition is the prevention of metastatis of malignant cells or to arrest or reverse the progression of malignant cells. This includes prophylactic treatment of those at risk of developing precancers and cancers.

The terms "therapeutically effective" and "pharmacologically effective" are intended to qualify the amount of each agent which will achieve the goal of improvement in disease severity and the frequency of incidence over treatment of each agent by itself, while avoiding adverse side effects typically associated with alternative therapies.

The term "subject" for purposes of treatment includes any human or animal subject having a neoplasia, such as cancer or precancer. For methods of prevention the subject is any human or animal subject, and preferably is a human subject who is at risk of developing a cancer. The subject may be at risk due to exposure to carcinogenic agents, being genetically predisposed to disorders characterized by unwanted, rapid cell proliferation, and so on. Besides being useful for human treatment, the compounds of the present invention are also useful for veterinary treatment of mammals, including companion animals and farm animals, such as, but not limited to dogs, cats, horses, cows, sheep, and pigs. Preferably, subject means a human.

The term "derivative" is intended to encompass compounds which are structurally related to the present invention or which possess the substantially equivalent activity to the parent heteroaryl-containing isoflavone compounds, as measured by the derivative's ability to inhibit activity in an in vitro estrogen dependent cell proliferation assay using human breast cells (such as MCF-7). By way of example, such compounds may include, but are not limited to, prodrugs thereof. Such compounds can be formed in vivo, such as by metabolic mechanisms.

Where the term alkyl is used, either alone or with other terms, such as haloalkyl or alkylaryl, it includes $C_1$ to $C_{10}$ linear or branched alkyl radicals, examples include methyl, ethyl, propyl, isopropyl, butyl, tert-butyl, and so forth. The term "haloalkyl" includes $C_1$ to $C_{10}$ linear or branched alkyl radicals substituted with one or more halo radicals. Some examples of haloalkyl radicals include trifluoromethyl, 1,2-dichloroethyl, 3-bromopropyl, and so forth. The term "halo" includes radicals selected from F, Cl, Br, and I.

The term aryl, used alone or in combination with other terms such as alkylaryl, haloaryl, or haloalkylaryl, includes such aromatic radicals as phenyl, biphenyl, and benzyl, as well as fused aryl radicals such as naphthyl, anthryl, phenanthrenyl, fluorenyl, and indenyl on so forth. The term "aryl" also encompasses "heteroaryls," which are aryls that have carbon and one or more heteroatoms, such as O, N, or S in the aromatic ring. Examples of heteroaryls include indolyl, pyrrolyl, and so on. "Alkylaryl" or "arylalkyl" refers to alkyl-substituted aryl groups such as butylphenyl, propylphenyl, ethylphenyl, methylphenyl, 3,5-dimethylphenyl, tert-butylphenyl and so forth.

The agents of the present invention may be administered orally, intravenously, intranasally, rectally, or by any means which delivers an effective amount of the active agent to the tissue or site to be treated. It will be appreciated that different dosages may be required for treating different disorders. An effective amount of an agent is that amount which causes a statistically significant decrease in neoplastic cell count, growth, or size. Neoplastic disorders responsive to the agents of the present invention include, but are not limited to, breast cancer.

The dosage form and amount can be readily established by reference to known treatment or prophylactic regiments. The amount of therapeutically active compound that is administered and the dosage regimen for treating a disease condition with the compounds and/or compositions of this invention depends on a variety of factors, including the age, weight, sex, and medical condition of the subject, the severity of the disease, the route and frequency of administration, the particular compound employed, the location of the unwanted proliferating cells, as well as the pharmacokinetic properties of the individual treated, and thus may vary widely. The dosage will generally be lower if the compounds are administered locally rather than systemically, and for prevention rather than for treatment. Such treatments may be administered as often as necessary and for the period of time judged necessary by the treating physician. One of skill in the art will appreciate that the dosage regime or therapeutically effective amount of the inhibitor to be administered may need to be optimized for each individual. The pharmaceutical compositions may contain active ingredient in the range of about 0.1 to 2000 mg, preferably in the range of about 0.5 to 500 mg and most preferably between about 1 and 200 mg. A daily dose of about 0.01 to 100 mg/kg body weight, preferably between about 0.1 and about 50 mg/kg body weight, may be appropriate. The daily dose can be administered in one to four doses per day.

The active agents may be administered along with a pharmaceutical carrier and/or diluent. The agents of the present invention may also be administered in combination with other agents, for example, in association with other chemotherapeutic or immunostimulating drugs or therapeutic agents. Examples of pharmaceutical carriers or diluents useful in the present invention include any physiological buffered medium, i.e., about pH 7.0 to 7.4 comprising a suitable water soluble organic carrier. Suitable water soluble organic carriers include, but are not limited to corn oil, dimethylsulfoxide, gelatin capsules, etc.

Also included in the family of heteroaryl-containing isoflavone compounds are the pharmaceutically acceptable salts thereof. The phrase "pharmaceutically acceptable salts" connotes salts commonly used to form alkali metal salts and to form addition salts of free acids or free bases. The nature of the salt is not critical, provided that it is pharmaceutically acceptable. Also included in the family of heteroaryl-containing isoflavone compounds are esters thereof. Esters of the heteroaryl-containing isoflavone compounds may be prepared by conventional methods known to those skilled in the art.

Suitable pharmaceutically acceptable acid addition salts of heteroaryl-containing isoflavone compounds may be prepared from an inorganic acid or from an organic acid. Examples of such inorganic acids are hydrochloric, hydrobromic, hydriodic, nitric, carbonic, sulfuric, and phosphoric acid. Appropriate organic acids may be selected from aliphatic, cycloaliphatic, aromatic, araliphatic, heterocyclic, carboxylic, and sulfonic classes of organic acids, examples of which include formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, ambonic, pamoic, methanesulfonic, ethanesulfonic, benzenesulfonic, pantothenic, 2-hydroxyethanesulfonic, toluenesulfonic, sulfanilic, cyclohexylaminosulfonic, stearic, algenic, β-hydroxybutyric, galactaric, and galacturonic acids.

Suitable pharmaceutically acceptable base addition salts of heteroaryl-containing isoflavone compounds include metallic salts made from aluminum, calcium, lithium, magnesium, potassium, sodium, and zinc. Alternatively, organic salts made from N,N'-dibenzylethylenediamine, chloroprocaine, choline, diethanolamine, ethylenediamine, meglumine (N-methylglucamine) and procaine may be used form base addition salts of the heteroaryl-containing isoflavone compounds. All of these salts may be prepared by conventional means from the corresponding heteroaryl-containing isoflavone compounds by reacting, for example, the appropriate acid or base with the heteroaryl-containing isoflavone compounds.

The phrase "adjunct therapy" (or "combination therapy"), in defining use of a compound of the present invention and one or more other pharmaceutical agent, is intended to embrace administration of each agent in a sequential manner in a regimen that will provide beneficial effects of the drug combination, and is intended as well to embrace co-administration of these agents in a substantially simultaneous manner, such as in a single formulation having a fixed ratio of these active agents, or in multiple, separate formulations for each agent.

There are large numbers of antineoplastic agents available in commercial use, in clinical evaluation and in pre-clinical development, which could be selected for treatment of cancers or other neoplasias by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents. Alternatively, other anti-neoplastic agents, such as metallomatrix proteases inhibitors may be used. Suitable agents which may be used in combination therapy will be recognized by those of skill in the art.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable carrier.

For intravenous, intramuscular, subcutaneous, or intraperitoneal administration, the compound may be combined with a sterile aqueous solution which is preferably isotonic with the blood of the recipient. Such formulations may be prepared by dissolving solid active ingredient in water containing physiologically compatible substances such as sodium chloride, glycine, and the like, and having a buffered pH compatible with physiological conditions to produce an aqueous solution, and rendering said solution sterile. The formulations may be present in unit or multi-dose containers such as sealed ampoules or vials.

Chemistry

Figure 1:
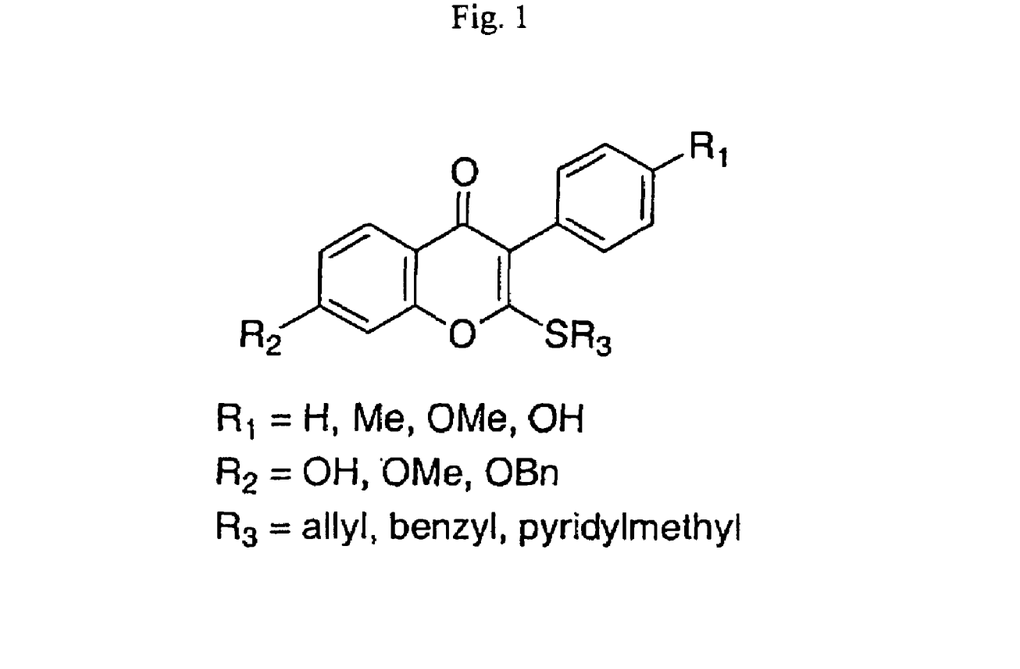
FIG. 1 shows the chemical structures of several representative nonsteroidal aromatase inhibitors.
Figure 3:
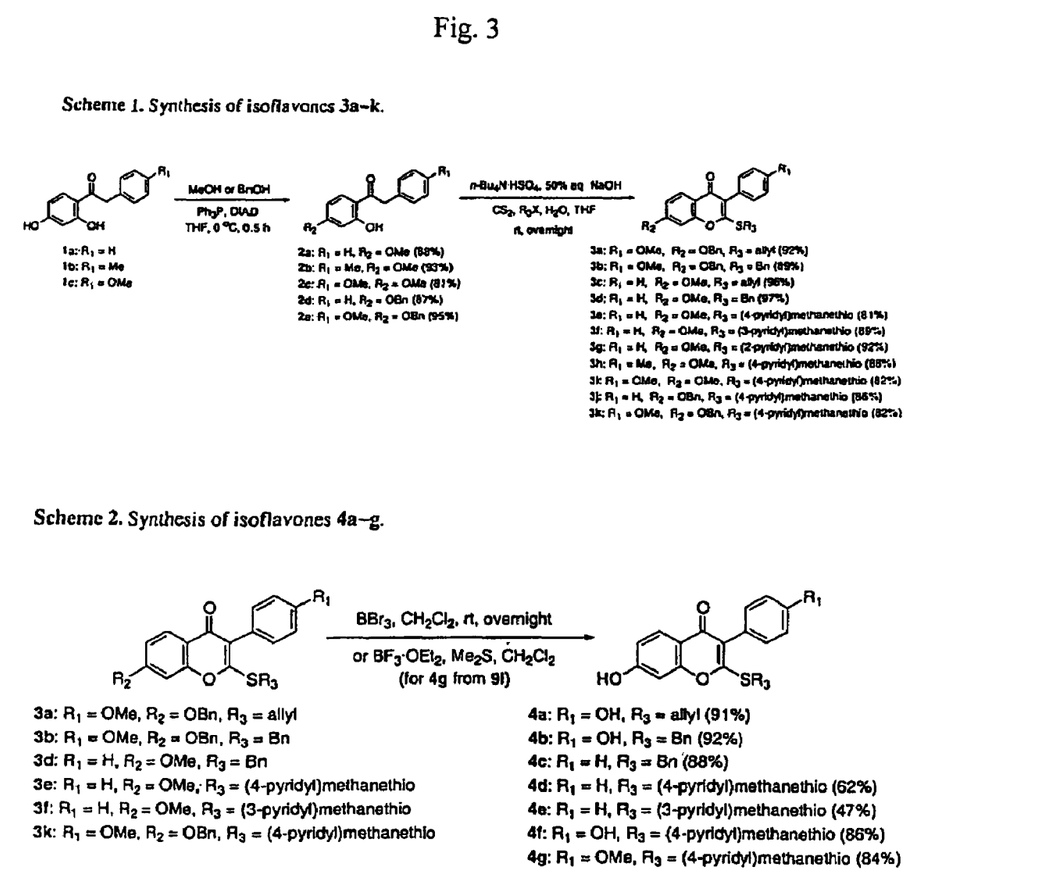
FIG. 3 shows two synthetic schemes used to prepare isoflavones.

We designed a library of 2,4',7-trisubstituted isoflavones as shown in FIG. 1. The synthesis of the target compounds was carried out as outlined in Scheme 1 and Scheme 2 (FIG. 3). The starting deoxybenzoins 1a-c are commercially available or can be easily prepared by known procedures. The 4-hydroxyl group of each 1 was selectively protected with methyl or benzyl group under Mitsunobu reaction conditions to give monoalkyl ethers 2a-e in excellent yields (Scheme 1). The treatment of each deoxybenzoin 2 was treated with carbon disulfide and an alkyl halide in a THF-aqueous NaOH solution in the presence of 10 mole % of tetrabutylammonium hydrogensulfate (n-$Bu_4$N.HSO) gave the corresponding 2-(alkylthio)isoflavone 3 in good to excellent yields. Dealkylation of selected compounds 3 was performed with boron tribromide in dichloromethane yielding hydroxy compounds 4a-f (Scheme 2). All attempts to prepare the 7-hydroxy-4'-methoxy analog 4g from 3k using typical debenzylation procedures (i.e. catalytic hydrogenation reactions with various hydrogen sources in the presence of palladium on carbon) failed presumably due to catalyst poisoning of the sulfide group of 3k. The use of one equivalent of boron tribromide at a low temperature also proved to be inefficient; only providing a mixture of 3k, 4f, and 4g. However, we found that $BF_3$.$OEt_2$-$Me_2$S reagent is mild enough to achieve the selective removal of benzyl, leaving the 4'-methoxy group intact to give 4g in a good yield. This reaction condition was originally reported as a mild alternative debenzylation method in order to avoid undesirable 1,4-conjugate addition of ethanethiol to substrates containing a Michael acceptor.

Biological Evaluation

Figure 2:
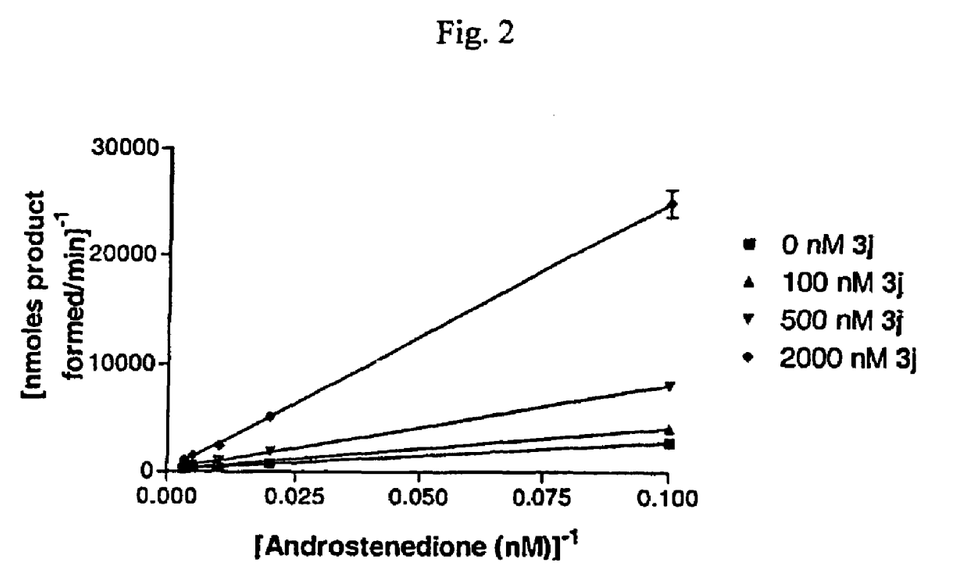
FIG. 2 shows Lineweaver-Burke plot and slope replot of compound 3j.

The aromatase assay was performed according to the modified method of the procedure previously reported by our laboratory, in which human placental microsomes were used as the aromatase source. $IC_{50}$ values of the compounds are shown in Table 1 and aminoglutethimide (AG) was used as a reference. The $IC_{50}$ value of BCA was also determined in our assay system for comparison. In order to examine the mode of aromatase inhibition, kinetic studies for selected compounds (3j, 4f, and 4g) were also performed, and their apparent K;

values are listed in Table 2 with apparent $K_m$ values and $K_i/K_m$ ratios. Lineweaver-Burk plot of compound 3j, the most potent analog in this series, is shown in FIG. 2.

TABLE 1

Aromatase Activity of isoflavones 3a-k and 4a-g

| Cmpd. | $R_1$ | $R_2$ | $R_3$ | $IC_{50}$ (µM) | Log $IC_{50}$ (nM) (±S.E)[a] |
|---|---|---|---|---|---|
| 3a | OMe | OBn | allyl | >100 | — |
| 3b | OMe | OBn | benzyl | >100 | — |
| 3c | H | OMe | allyl | >100 | — |
| 3d | H | OMe | benzyl | >100 | — |
| 3e | H | OMe | (4-pyridyl)methyl | 1.6 | 3.21 ± 0.11 |
| 3f | H | OMe | (3-pyridyl)methyl | 9.2 | 3.96 ± 0.16 |
| 3g | H | OMe | (2-pyridyl)methyl | >100 | — |
| 3h | Me | OMe | (4-pyridyl)methyl | 3.0 | 3.48 ± 0.05 |
| 3i | OMe | OMe | (4-pyridyl)methyl | 2.0 | 3.36 ± 0.30 |
| 3j | H | OBn | (4-pyridyl)methyl | 0.21 | 2.33 ± 0.03 |
| 3k | OMe | OBn | (4-pyridyl)methyl | 0.53 | 2.72 ± 0.11 |
| 4a | OH | OH | allyl | N.D.[b] | — |
| 4b | OH | OH | benzyl | N.D.[b] | — |
| 4c | H | OH | benzyl | N.D.[b] | — |
| 4d | H | OH | (4-pyridyl)methyl | 0.61 | 2.79 ± 0.11 |
| 4e | H | OH | (3-pyridyl)methyl | 3.6 | 3.56 ± 0.06 |
| 4f | OH | OH | (4-pyridyl)methyl | 0.28 | 2.44 ± 0.07 |
| 4g | OMe | OH | (4-pyridyl)methyl | 0.22 | 2.34 ± 0.04 |
| [c]AG | | | | 2.8 | 3.45 ± 0.05 |
| BCA | | | | 34 | 4.53 ± 0.06 |

[a]$IC_{50}$ values were calculated by a nonlinear regression analsys (GraphPad Prizm). Each dose-response curve contained ten concentrations, each in triplicate.
[b]Not determined.
[c]Aminoglutethimide

TABLE 2

Enzyme kinetic parameters for selected isoflavones and reference compounds

| Compound | Apparent $K_i$ (µM) (±S.E) | Apparent $K_m$ (µM) (±S.E) | $K_i/K_m$ |
|---|---|---|---|
| 3j | 0.22 ± 0.02 | 0.13 ± 0.01 | 1.69 |
| 4f | 0.31 ± 0.02 | 0.11 ± 0.07 | 2.82 |
| 4g | 0.26 ± 0.02 | 0.10 ± 0.02 | 2.60 |
| AG | 1.41 ± 0.10 | 0.09 ± 0.01 | 15.7 |
| BCA | 12 ± 5[a] | — | — |

[a]From literature

Results and Discussion

Bioassay results showed that the analogs lacking a pyridyl group (3a-d and 4a-c) are less active than those containing a pyridine moiety. It was also obvious that the position of the nitrogen atom of pyridyl moiety affected the inhibitory activity. 4-Pyridyl analog 3e ($IC_{50}$=1.6 µM) exerts ~6-fold more potent inhibitory activity than 3-pyridyl analog 3f ($IC_{50}$=9.2 µM). In the 7-hydroxy analogs; the 4-pyridyl analog 4d ($IC_{50}$=0.61 µM) is ~6-fold more potent than 3-pyridyl analog 4e ($IC_{50}$=3.6 µM). Although the precise mechanisms of action of these compounds are not clear at present, the pyridyl moiety is thought to be involved in coordination with the heme iron of aromatase. Based on this hypothesis, it may be postulated that the nitrogen atom of the 4-pyridyl group may he in the more favorable position to coordinate to the heme iron than that of the 3- or 2-pyridyl group.

In addition, the 7-hydroxy compounds, 4d ($IC_{50}$=0.61 µM) and 4e ($IC_{50}$=3.6 µM), exhibit ~3-fold greater inhibitory activities than their 7-methoxy analogs, 3e ($IC_{50}$=1.6 µM) and 3g ($IC_{50}$=9.2 µM), respectively. This result suggests that the presence of a hydrogen-bond donor at the 7-position might provide a favorable interaction with the enzyme. With regard to 4'-substituent, while the 4'-methyl analog 3h ($IC_{50}$=3.0 µM) appears less potent than the others, 4'-hydrogen analog 3e ($IC_{50}$=1.6 µM) shows a slightly higher activity than 4'-methoxy analog 3h ($IC_{50}$=2.0 µM). However, the relatively small difference in their activities may indicate that the effects of 4'-substitutent may not be critical for the activity. Interestingly, this trend is not observed in the 7-hydroxy analogs, 4g and 4d; i.e. in the presence of 7-hydroxy group, 4'-methoxy analog 4g ($IC_{50}$=0.22 µM) is more potent than 4'-hydrogen analog 4d ($IC_{50}$=0.61 µM). Interestingly, the difference in their potency between 4'-methoxy and 4'-hydrogen substituents in the 7-hydroxy analogs appears to be greater than that observed in the 7-methoxy analogs. In addition, the potency of 4',7-dihydroxy analog 4f ($IC_{50}$=0.28 µM) was comparable to that of 7-hydroxy-4'-methoxy analog 4g ($IC_{50}$=0.22 µM), but ~2-fold greater than that of 7-hydroxy-4'-hydrogen analog 4d ($IC_{50}$=0.61 µM). This result suggests that the presence of a proton acceptor at the 4'-position in the 7-hydroxy analogs may be beneficial for the aromatase inhibitory activity.

To our surprise, 7-benzyloxy analog 3k ($IC_{50}$=0.53 µM), originally prepared as a precursor of compound 4g, showed a potent inhibitory activity. This result was unexpected because the compound was thought to be too bulky to fit in the active site of the enzyme due to the benzyl group. The 7-benzyloxy-4'-hydrogen analog 3j ($IC_{50}$=0.21 µM) exerts a enhanced potency over 7-benzyloxy-4'-methoxy analog 3k and ~8-fold greater than 4'-hydrogen-7-methoxy analog 3e (7-OBn versus 7-OMe). Also, 3j is 13-fold and 162-fold more potent than AG and BCA, respectively, in our assay system in terms of $IC_{50}$ values.

In kinetic studies, compounds 3j, 4f, and 4g demonstrated typical competitive type of inhibition in the Lineweaver-Burke plots (FIG. 2, data for 4f and 4g are not shown), suggesting that they may inhibit aromatase activity by competing with androstenedione for the substrate binding site of the enzyme. $K_i/K_m$ ratios of compounds 3j, 4f, and 4g were calculated as a relative inhibitory potency (Table 2), and the same order of potency (3j>4g>4f) was observed as in the $IC_{50}$ studies. As reflected by its $K_i/K_m$ ratio, compound 3j is the most potent in this series and is ~10-fold more potent than AG. 3j also demonstrates 50-fold enhancement in potency compared to our natural product lead, BCA.

Experimental Section

Unless otherwise noted, chemicals were commercially available and used as received without further purification. Moisture sensitive reactions were carried out under a dry argon atmosphere in flame-dried glassware. Solvents were distilled before use under argon. Tetrahydrofuran was distilled from sodium metal in the presence of benzophenone; dichloromethane was distilled from calcium hydride. Thin layer chromatography was performed on precoated silica gel F254 plates (Whatman). Silica gel column chromatography was performed using silica gel 60A (Merck, 230-400 Mesh). Melting points were determined in open glass capillaries using a Thomas Hoover apparatus and are uncorrected. Infrared spectra were recorded on a Nicola Protege 460 spectrometer using KBr pellets. High-resolution electrospray ionization mass spectra were obtained on the Micromass QTOF Electrospray mass spectrometer at The Ohio State Chemical Instrumentation Center. All the NMR spectra were recorded on a Brukcr DPX 250, or Brukcr DRX 400 model spectrometer in either DMSO-$d_6$ or $CDCl_3$. Chemical shifts (δ) for $^1H$ NMR spectra are reported in parts per million to residual solvent protons. Chemical shifts (δ) for $^{13}C$ NMR spectra are reported in parts per million relative to residual solvent carbons.

General Procedure for the Preparation of 4-alkoxydeoxybenzoins (2a-e). To a solution of 2-aryl-1-(2,4-dihydroxyphenyl)ethanone (31.0 mmol) and alcohol (32.55 mmol) in THF (150 mL) was added triphenylphosphine (8.538 g, 32.55 mmol), followed by diisopropyl azodicarboxylate (6.41 mL, 32.55 mmol) at 0° C., and the resulting yellow solution was stiffed at 0° C. for 10 min. The solvent was removed under reduced pressure, and the oily residue was directly purified by silica gel column chromatography (eluting with EtOAc:hexane, 1:4) and recrystallization (EtOAc and hexane) to yield desired product.

1-(2-Hydroxy-4-methoxyphenyl)-2-phenylethanone (2a). Using the previous procedure and starting from 1-(2,4-dihydroxyphenyl)-2-phenylethanone (7.08 g, 31.0 mmol) and methanol (1.32 mL, 32.55 mmol), 6.60 g (88%) of the title compound was obtained as a white solid: mp 87-88° C. (lit. 92° C.); IR (KBr) 1635, 1620, 1589, 1437, 1350, 1291, 1230, 1206, 1127, 1021, 958, 802, 739, 729, 551 $cm^{-1}$; $^1H$ NMR (400 MHz, $CDCl_3$) δ 12.71 (br s, 1H), 7.74 (d, J=8.7 Hz, 1H), 7.31-7.34 (m, 2H), 7.23-7.26 (m, 3H), 6.40-6.44 (m, 2H), 4.20 (s, 2H), 3.81 (s, 3H); $^{13}C$ NMR (100 MHz, $CDCl_3$) δ 202.38, 166.61. 166.30, 134.82, 132.47, 129.76, 129.16, 127.50, 113.58, 108,27, 101.44, 56.00, 45.27.

1-(2-Hydroxy-4-methoxyphenyl)-2-(4-methylphenyl)ethanone (2b). Using the previous procedure and starling from 1-(2,4-dihydroxyphenyl)-2-(4-methylphenyl)ethanone (7.51 g, 31.0 mmol) and methanol (1.32 mL, 32.55 mmol), 7.38 g (93%) of the title compound was obtained as a white solid: mp (EtOAc/hexane) 71-72° C.; IR (KBr) 1639, 1623, 1590, 1516, 1508, 1439, 1388, 1355, 1268, 1231, 1205, 1131, 10.33, 1010, 957, 800, 780, 571, 504, 491 $cm^{-1}$; $^1H$ NMR (400 MHz, $CDCl_3$) δ 12.72 (br s, 1H), 7.73 (d, J=8.6 Hz, IH), 7.24-7.14 (m, 4H), 6.43-6.40 (m, 2H), 4.1.5 (s, 2H), 3.81 (s, 3H), 2.31 (s, 3H); $^{13}C$ NMR (100 MHz, $CDC_3$) δ 202.63, 166.56, 166.28, 137.14, 132.47. 131.71, 129.87, 129.61. 113.60, 108.20, 101.43, 55.98, 44.89, 21.48; HRMS calculated for $C_{16}H_{16}NaO_1$ $(M+Na)^+$ 279.0997. found 279.0989.

1-(2-Hydroxy-4-methoxyphenyl)-2-(4-methoxyphenyl)ethanone (2c). Using the previous procedure and starting from 1-(2,4-dihydroxyphenyl)-2-(4-methoxyphenyl)ethanone (8.0 g, 11.0 mmol) and methanol (1.32 mL, 32.55 mmol), 6.8.5 g (81%) of the title compound was obtained as a white solid: mp 101-102° C. (lit. 104° C.); IR (KBr) 1637, 1611, 1513, 1459, 1346. 1301, 1237, 1174, 1148, 1026 797, 787, 626, 522 $cm^{-1}$; $^1H$ NMR (400 MHz, $CDCl_3$) δ 12.72 (br s, 1H), 7.73 (d, J=8.8 Hz, 1H), 7.17 (d, J=8.6 Hz. 2H), 6.86 (d, J=8.6 Hz, 2H), 6.40-6.44 (m, 2H), 4.13 (s, 2H), 3.81 (s, 3H), 3.77 (s, 3H); $^{13}C$ NMR (100 MHz, $CDCl_3$) δ 202.73, 166.55, 166.27, 159.07, 132.42, 130.78, 126.73, 114.61, 113.53, 108.21, 101.42, 55.99, 55.67, 44.37.

1-[2-Hydroxy-4-(phenylmethoxy)phenyl]-2-phenylethanone (2d). Using the previous procedure and starting from 1-(2,4-dihydroxyphenyl)-2-phenylethanone (7.08 g, 31.0 mmol) and benzyl alcohol (3.37 mL, 32.55 mmol), 8.62 g (87%) of the title compound was obtained as a white solid: mp 106-108° C. (lit. 104-105° C.); IR (KBr) 1620, 1572, 1500, 1389, 1352, 1270, 1230, 1192, 1134, 1000, 974, 830, 760, 729, 697, 628, 561 $cm^{-1}$; $^1H$ NMR (400 MHz, $CDCl_3$) δ 12.69 (br s, 1H), 7.48 (d, J=8.7 Hz, 1H), 7.25-7.39 (m, 10H), 6.49-6.51(m, 2H), 5.07 (s, 2H), 4.20 (s, 2H); $^{13}C$ NMR (100 MHz, $CDCl_3$) δ 202.41, 166.20, 16.5.68, 136.22, 134.79, 132.53, 129.76, 129.17, 129.14, 128.76, 127.95, 127.51, 113.77, 108.75, 102.47, 70.66, 45.28; HRMS calculated for $C_{21}H_{18}NaO_3$ $(M+Na)^+$ 341.1154, found 341.1136.

1-[2-Hydroxy-4-(phenylmethoxy)phenyl]-2-(4-methoxyphenyl)ethanone (2e). Using the previous procedure and starting from 1-(2,4-dihydroxyphenyl)-2-(4-methoxyphenyl)ethanone (8.0 g, 31.0 mmol) and benzyl alcohol (3.37 mL, 32.55 mmol), 10.23 g (95%) of the title compound was obtained as a white solid: mp 97-98° C. (lit. 93-95° C.); IR (KBr) 1635, 1611, 1512, 1496, 1387, 1351, 1289, 1227, 1173, 1131, 1029, 994, 948, 842, 830, 791, 745, 725, 695, 535 $cm^{-1}$; $^1H$ NMR (250 MHz, $CDCl_3$) δ 12.73 (s, 1H), 7.75 (d, J=9.6 Hz, 1H), 7.33-733-7.40 (m, 5H), 7.18 (d, J=8.5 Hz, 2H), 6.87 (d, J=8.5 Hz, 2H), 6.53-6.49 (m, 2H), 5.07 (s, 2H), 4.14 (s, 2H), 3.78 (s, 3H); $^{13}C$ NMR (69.3 MHz, $CDCl_3$) δ 202.77, 166.19, 165.63, 159.10, 136.26, 132.51, 130.82, 129.15, 128.77, 127.97, 126.71, 114.63, 113.73, 108.71, 102.48, 70.6.5, 55.69, 44.38; HRMS calculated for $C_{22}H_{20}NaO_4$ $(M+Na)^+$ 371.1259, found 371.1265.

General Procedure for the Preparation of 2-Alkylthio-isoflavones (3a-k) from 2'-hydroxydeoxybenzoins. To a stirred mixture of a deoxybenzoin (1 mmol), carbon disulfide (0.6 mL, 10 mmol), alkyl halide (2.2 mmol), and tetrabutylammonium hydrogensulfate (34 mg, 0.1 mmol) in THF (3 mL) and water (1 mL) was slowly added 10 M solution of NaOH in water (1.2 mL, 12 mmol) at room temperature. A slight exothermic reaction and a color change of the mixture were observed. The resulting mixture was vigorously stirred at room temperature for several hours, and the product was extracted with ethyl acetate (2×10 mL). The combined organic layer was washed with water (10 mL) and then with brine (10 mL), dried over $MgSO_4$, and filtered. The filtrate was concentrated under reduced pressure, and the residue was purified by silica gel column chromatography (eluting with $MeOH/CHCl_3$ or EtOAc/hexane) and recrystallization (EtOAc/hexane) to yield desired product.

3-(4-Methoxyphenyl)-7-(phenylmethoxy)-2-[(propen-2-yl)thiol-]4H-1-benzopyran-4-one (3a). Using 1-[2-hydroxy-4-(phenylmethoxy)phenyl]-2-(4-methoxyphenyl)ethanone (0.348 g, 1.0 mmol) as a starting deoxybenzoin and ally bromide (0.208 mL, 2.4 mmol) as an alkyl halide, 0.396 g (92%) of the title compound was obtained as a white solid: mp 101-102° C.; IR (KBr) 1618, 1509, 1438, .1363, 1342, 1291, 1247, 1176, 1152, 1101, 1030, 944, 821, 740, 696 $cm^{-1}$; $^1H$ NMR (250 MHz, $CDCl_3$) δ 8.13 (d, J=8.8 Hz, 1H), 7.33-7.46 (m, 5H), 7.25 (d, J=8.7 Hz, 2H), 7.02 (dd, J=8.9. 2.3 Hz, 1H), 6.95 (d, J=8.7 Hz, 2H), 6.89 (d, J=2.3 Hz, 1H), 5.87 (ddt. J=16.9, 10.0, 6.9 Hz, 1H), 5.25 (dd, J=16.9, 1.2 Hz; 1H), 5.11-5.06 (m, 3H), 3.82 (s, 3H), 3.69 (d, J=6.9 Hz, 2H); $^{13}C$ NMR (62.9 MHz, $CDCl_3$) δ 174.34, 163.40, 163.10, 159.93, 158.38, 136.17, 133.30, 132.30, 129.20, 128.84, 128.48, 127.95, 124.64, 122.88. 119.22, 117.86, 114.96, 114.36, 101.29, 71.01, 55.65, 34.59; HRMS calculated for $C_{26}H_{22}NaO_1S$ $(M+Na)^+$ 453.1137, found 453.1123. Anal. ($C_{26}H_{22}O_4S.0.3H_2O$) C, H.

3-(4-Methoxyphenyl)-7-(phenylmethoxy)-2-[(phenylmethyl)thio]-4H-1-benzopyran-4-one (3b). Using 1-[2-hydroxy-4-(phenylmethoxy)phenyl]-2-(4-methoxyphenyl)ethanone (0.348 g, 1.0 mmol) as a starting deoxybenzoin and benzyl bromide (0.274 mL, 2.3 mmol) as an alkyl halide, 0.427 g (89%) of the title compound was obtained as a white solid: mp 131-1.32° C.; IR (KBr) 1618, 1508, 1438. 1364, 1247, 1176, 1029, 822, 697 $cm^{-1}$; $^1H$ NMR (250 MHz, CDCl$_3$) δ 8.14 (d, J=8.9 Hz, 1H), 7.22-7.48 (m, 10H), 7.21 (d, J=8.7 Hz, 2H), 7.03 (dd, J=8.9, 2.3 Hz, 1H), 6.93 (d, J=8.7 Hz, 2H), 6.89 (d, J=2.3 Hz, 1H), 5.17 (s, 2H), 4.28 (s, 2H), 3.81 (s, 3H); $^{13}$C NMR (62.9 MHz, CDCl$_3$) δ 174.33, 163.61, 163.09, 159.91, 158.38, 136.61, 136.17, 132.25, 129.33, 129.25, 129.18, 128.88, 128.49, 128.15, 127.96, 124.52, 122.42, 117.82, 115.03, 114.36, 101.25, 71.01, 55.65, 36.17; HRMS calculated for C$_{30}$H$_{24}$NaO$_4$S (M+Na)$^+$ 503.1293, found 503.1258. Anal. (C$_{30}$H$_{24}$O$_4$S.0.1H$_2$O) C, H.

7-Methoxy-3-phenyl-2-[(propen-2-yl)thio]-4H-1-benzopyran-4-one (3c). Using 1-(2-hydroxy-4-methoxyphenyl)-2-phenylethanone (0.242 g, 1.0 mmol) as a starting deoxybenzoin and ally bromide (0.190 mL, 2.2 mmol) as an alkyl halide, 0.314 g (96%) of the title compound was obtained as a white solid (Method B): mp 117-118° C.; IR (KBr) 1635, 1615, 1585, 1546, 1503, 1435, 1373, 1345, 1252, 1197, 1108, 1017, 942, 922, 831, 753, 701, 662 cm$^{-1}$; $^1$H NMR (400 MHz, CDCl$_3$) δ 8.13 (d, J=8.9 Hz, 1H), 7.30-7.44 (m, 5H), 6.96 (dd, J=8.9, 2.4 Hz, IH), 6.81 (d, J=2.3 Hz, 1H), 5.83-5.94 (m, 1H), 5.27 (dd, J=16.9, 1.2 Hz, 1H), 5.14 (dd, J=10.1, 0.8 Hz, 1H), 3.91 (s, 3H), 3.70 (d, J=6.9 Hz, 2H); $^{13}$C NMR (62.9 MHz, CDCl$_3$) δ 174.21, 164.12, 163.40, 158.50, 133.20, 132.61, 131.08, 128.82, 128.68, 128.39, 123.35, 119.27, 117.69, 114.51, 100.13, 56.31, 34.54; HRMS calculated for C$_{19}$H$_{16}$NaO$_3$S (M+Na)$^+$ 347.0718, found 347.0705. Anal. (C$_{19}$H$_{16}$O$_3$S.0.2H$_2$O) C, H.

7-Methoxy-3-phenyl-2-[(phenylmethyl)thio]-4H-1-benzopyran-4-one (3d). Using 1-(2-hydroxy-4-methoxyphenyl)-2-phenylethanone (0.242 g, 1.0 mmol) as a starting deoxybenzoin and benzyl bromide (0.262 mL, 2.2 mmol) as an alkyl halide, 0.365 g (97%) of the title compound was obtained as a white solid: mp 153-154° C.; IR (KBr) 1636, 1617, 1586, 1546, 1502, 1438, 1373, 1341, 1252, 1205, 1106, 1016, 942, 831, 699, 661 cm$^{-1}$; $^1$H NMR (400 MHz, CDCl$_3$) δ 8.12 (d, J=8.9 Hz, 1H), 7.22-7.41 (m, 10H), 6.95 (dd, J=8.9, 2.4 Hz, 1H), 6.81 (d, J=2.3 Hz, 1H), 4.30 (s, 2H), 3.91 (s, 3H); $^{13}$C NMR (62.9 MHz, CDCl$_3$) δ 174.22, 164.10, 163.54, 158.48, 136.51, 132.52, 131.04, 129.32, 129.17, 128.81, 128.66, 128.39, 128.17, 122.97, 117.70, 114.49, 100.19, 56.31, 36.17; HRMS calculated for C$_{23}$H$_{18}$NaOS (M+Na)$^+$ 397.0874, found 397.0856. Anal. (C$_{23}$H$_{18}$O$_3$S.0.1H$_2$O) C, H.

7-Methoxy-3-phenyl-2-[(4-pyridylmethyl)thiol]-4H-1-benzopyran-4-one (3e). Using 1-(2-hydroxy-4-methoxyphenyl)-2-phenylethanone (0.242 g, 1.0 mmol) as a starting deoxybenzoin and 4-(bromomethyl)pyridine hydrobromide (0.557 g, 2.2 mmol) as an alkyl halide, 0.305 g (81%) of the title compound was obtained as a white solid: mp 136-137 C; IR (KBr) 1634, 1622, 1600, 1549, 1497, 1433, 1369, 1257, 1200, 1098, 1067, 1013, 943, 831, 775, 756, 703, 658, 570 cm+$^{-1}$; $^1$H NMR (400 MHz. CDCl$_3$) δ 8.53 (dd, J=4.5, 1.5 Hz, 2H), 8.09 (d, J=8.9 Hz, 1H), 7.33-7.42 (m, 3H), 7.24-7.27 (m, 4H), 6.93 (dd, J=8.9, 2.4 Hz, 1H), 6.70 (d, J=2.3 Hz, 1H), 4.21 (s, 2H), 3.87 (s, 3H); $^{13}$C NMR (100 MHz. CDCl$_3$) δ 174.09, 164.21, 161.95, 158.33, 150.45, 146.38, 132.22, 130.95, 128.89, 128.86, 128.46, 124.04, 123.58, 117.59, 114.50, 100.16, 56.31, 34.79; HRMS calculated for C$_{22}$H$_{17}$NNaO$_3$S (M+Na)$^+$ 398.0827, found 398.0818. Anal. (C$_{22}$H$_{17}$NO$_3$S.0.2H$_2$O) C, H, N.

7-Methoxy-3-phenyl-2-[(3-pyridylmethyl)thio]-4H-1-benzopyran4-one (31). Using 1-(2-hydroxy-4-methoxyphenyl)-2-phenylethanone (0.242 g, 1.0 mmol) as a starting deoxybenzoin and 3-(bromomethyl)pyridine hydrobromide (0.557 g, 2.2 mmol) as an alkyl halide, 0.334 g (89%) of the title compound was obtained as a white solid: mp 151.5-152° C.; IR (KBr) 1635, 1617, 1.585, 1547, 1503, 1438, 1427, 1373, 1344, 1253, 1203, 1108, 1017, 943, 831, 754, 701, 662 cm$_{-1}$; $^1$H NMR (400 MHz. CDCl$_3$) δ 8.62 (br s, 1H), 8.49 (d, J=4.3 Hz, 1H) 8.10 (d, J=8.9 Hz, 1H), 7.69 (d, J=7.9 Hz, 1H), 7.35-7.41 (m, 3H), 7.23-7.28 (m, 3H), 6.95 (dd, J=8.9, 2.1 Hz, 1H), 6.79 (d, J=2.1 Hz, 1H), 4.27 (s, 2H), 3.91 (s, 3H); $^{13}$C NMR (100 MHz, CDCl$_3$) δ 174.11, 164.24, 162.30, 158.42, 150.24, 149.35, 136.81, 132.93, 132.29, 130.96, 128.86, 128.80, 128.41, 124.11, 12.3.46, 117.60, 114.66, 100.10, 56.34, 33.21; HRMS calculated for C$_{22}$H$_{17}$NNaO$_3$S (M+Na)$^+$ 398.0827, found 398.0840. Anal. (C$_{22}$H$_{17}$NO$_3$S.1.0H$_2$O) C, H, N.

7-Methoxy-3-phenyl-2-[(2-pyridylmethyl)thio]-4H-1-benzopyran-4-one (3g). Using 1-(2-hydroxy-4-methoxyphenyl)-2-phenylethanone (0.242 g, 1.0 mmol) as a starting deoxybenzoin and 2-(Bromomethyl)pyridine hydrobromide (0.557 g, 2.2 mmol) as an alkyl halide, 0.345 g (92%) of the title compound was obtained as a white solid: mp 168.5-169° C.; IR (KBr) 1634, 1617, 1586, 1546, 1502, 1431, 1373, 1344, 1252, 1202, 1153, 1106, 1016, 943, 831, 782, 752, 698, 661 cm$^{-1}$; $^1$H NMR (400 MHz, DMSO-d$_6$) δ 8.47 (ddd, J=4.9, 1.7, 0.9 Hz, 1H), 7.88 (d, J=8.8 Hz, 1H), 7.74 (dt, J=7.7, 1.8 Hz, 1H), 7.49 (d, J=7.8 Hz, 1H), 7.30-7.39 (m, 3H), 7.34 (ddd, J=7.6, 4.9, 0.9 Hz, 1H), 7.17-7.19 (m, 3H), 7.03 (dd, J=8.8, 2.4 Hz, 1H), 4.54 (s, 2H), 3.88 (s, 3H); $^{13}$C NMR (100 MHz, DMSO-d$_6$) δ 173.33, 164.34, 163.86, 158.54, 157.30, 150.20, 137.88, 133.14, 131.46, 129.03, 128.86, 127.75, 124.04, 123.43, 122.40, 117.23, 115.46, 101.23, 57.02, 37.39; HRMS calculated for C$_{22}$H$_{17}$NNaO$_3$S (M+Na)$^+$ 398.0827, found 398.0819. Anal. (C$_{22}$H$_{17}$NO$_3$S.0.1H$_2$O) C, H, N.

7-Methoxy-3-(4-methylphenyl)-2-[(4-pyridylmethyl)thio]-4H-1-benzopyran-4-one (3h). Using 1-(2-hydroxy-4-methoxyphenyl)-2-(4-methylphenyl)ethanone (0.256 g, 1.0 mmol) as a starting deoxybenzoin and 4-(bromomethyl)pyridine hydrobromide (0.557 g, 2.2 mmol) as an alkyl halide, 0.335 g (86%) of the title compound was obtained as a white solid: mp 157-160° C.; IR (KBr) 1628, 1598, 1585, 1543, 1497, 1434, 1373, 1343, 1254, 1198, 1182, 1099, 1016, 936, 837, 814 cm$^{-1}$; $^1$H NMR (400 MHz, CDCl$_3$) δ 8.52 (d, J=5.6 Hz, 2H), 8.08 (d, J=8.9 Hz, 1H), 7.26 (d, J=5.5 Hz, 2H), 7.21 (d, J=7.8 Hz, 2H), 7.14 (d, J=7.9 Hz, 2H), 6.92 (dd, J=8.9, 2.1 Hz, 1H), 6.69 (d, J=2.0 Hz, 1H), 4.20 (s, 2H), 3.87 (s, 3H), 2.35 (s, 3H); $^{13}$C NMR (100 MHz, CDCl$_3$) δ 174.20, 164.15, 161.79, 158.32, 150.46, 146.37, 138.72, 130.75, 129.67, 129.17, 128.46, 124.05, 123.46, 117.58, 114.44, 100.14, 56.29, 34.79, 21.85; HRMS calculated for C$_{23}$H$_{19}$NNaO$_3$S (M+Na)$^+$ 412.0983, found 398.1004. Anal. (C$_{23}$H$_{19}$NO$_3$S.0.1H$_2$O) C, H, N.

7-Methoxy-3-(4-methoxyphenyl)-2-[(4-pyridylmethyl)thio]-4H-1-benzopyran-4-one (3i). Using 1-(2-hydroxy-4-methoxyphenyl)-2-(4-methoxyphenyl)ethanone (0.272 g, 1.0 mmol) as a starting deoxybenzoin and 4-(bromomethyl)pyridine hydrobromide (0.557 g, 2.2 mmol) as an alkyl halide, 0.332 g (82%) of the title compound was obtained as a white solid: mp 140-141° C.; IR (KBr) 1622, 1609, 1549, 1510, 1434, 1369, 1343, 1288, 1250, 1199, 1180, 1099, 1024, 961, 945, 835, 821, 778 cm$^{-1}$; $^1$H NMR (400 MHz, CDCl$_3$) δ 8.53 (d, J=5.8 Hz, 2H), 8.08 (d, J=8.9 Hz, 1H), 7.27 (d, J=5.7 Hz, 2H), 7.18 (d, J=8.6 Hz, 2H), 6.92-6.94 (m, 3H), 6.69 (d, J=2.1 Hz, 1H), 4.21 (s, 2H), 3.88 (s, 3H), 3.80 (s. 3H); $^{13}$C NMR (100 MHz, CDCl$_3$) δ 174.29, 164.14, 161.82, 160.05, 158.32, 150.42, 146.46, 132.16, 128.48, 124.24, 124.06, 123.11, 117.57, 114.42, 114.40, 100.13, 56.29, 55.65, 34.82; HRMS calculated for C$_{23}$H$_{19}$NNaO$_4$S (M+Na)$^+$ 428.0932, found 428.0949. Anal. (C$_{23}$H$_{19}$NO$_4$S.0.1H$_2$O) C, H, N.

3-Phenyl-7-(phenylmethoxy)-2-[(4-pyridylmethyl)thin]-4!I-1-benzopyran-4-one (3j). Using 1-[2-hydroxy-4-(phenylmethoxy)phenyl]-2-phenylethanone (0.318 g, 1.0 mmol) as a starting deoxybenzoin and 4-(bromomethyl)pyridine hydrobromide (0.557 g, 2.2 mmol) as an alkyl halide, 0.386 g (86%) of the title compound was obtained as a pale yellow solid: mp 169-170° C.; IR (KBr) 1619, 1599, 1584, 1540, 1491, 1440, 1372, 1344, 1259, 1196, 1157, 1099, 991, 943, 836, 819, 781, 747, 695 cm$^{-1}$; $^1$H NMR (400 MHz, CDCl$_3$) δ 8.51 (dd, J=4.5, 1.6 Hz., 2H), 8.11 (d, J=8.9 Hz, 1H), 7.34-7.45 (m, 8H), 7.72-7.26 (m, 4H), 7.03 (dd, J=8.9, 2.3 Hz, 1H), 6.78 (d, J=2.3 Hz, 1H), 5.1.5 (s, 2H), 4.19 (s, 2I-I). $^{13}$C NMR (100 MHz, CDCl$_3$) δ 174.03, 163.22, 161,99, 158.23, 150.61, 146.23, 136.06, 132.19, 130.94, 129.25, 128.90, 128.88, 128.57, 127.88, 123.94, 123.59, 117.80, 115.11, 101.25, 71.03, 34.78; HRMS calculated for $C_{28}H_{21}NNaO_3S$ (M+Na)$^+$ 474.1140, found 474.1136. Anal. ($C_{28}H_{21}NO_3S.0.1H_2O$) C, H, N.

3-(4-Methoxyphenyl)-7-(phenylmethoxy)-2-[(4-pyridylmethyl)thio]-4H-1-benzopyran-4-one (3k). Using 1-[2-hydroxy-4-(phenylmethoxy)phenyl]-2-(4-methoxyphenyl)cthanonc (0.348 g, 1.0 mmol) as a starting deoxybenzoin and 4-(bromomethyl)pyridine hydrobromide (0.557 g, 2.2 mmol) as an alkyl halide, 0.402 g (84%) of the title compound was obtained as a white solid: mp 169.5-170.5° C.; IR (KBr) 1616, 1539, 1509, 1440, 1414, 1371, 1342, 1294, 1251, 1197, 1173, 1156, 1100, 1029, 991. 943. 824, 735, 697, 665 cm$^{-1}$; $^1$H NMR (400 MHz., DMSO-d$_6$) δ 8.44 (d, J=5.8 Hz, 2H), 7.87 (d, J=8.8 Hz, 1H), 7.35-7.49 (m, 7H), 7.30 (d, J=2.3 Hz, 1H), 7.08-7.12 (m, 3H), 6.93 (d, J=8.7 Hz, 2H), 5.26 (s, 2H), 4.39 (s, 2H), 3.75 (s, 3H); $^{13}$C NMR (100 MHz, DMSO-d$_6$) δ 173.39, 163.30, 162.91, 159.90, 158.31, 150.68, 147.69, 136.95, 132.64, 129.46, 129.08, 128.82, 127.86, 124.79, 124.70, 122.37, 117.32, 115.95, 114.55, 102.25, 70.95, 55.96, 34.03; HRMS calculated for $C_{29}H_{23}NNaO_4S$ (M+Na)$^+$ 504.1245, found 504.1238. Anal. ($C_{29}H_{23}NO_4S.0.2H_2O$) C, H, N.

General Procedure for Dealkylation using Boron Tribromide (4a-g). To a stirred solution of 2-substituted 7-alkoxy-3-aryl-4H-1-benzopyran-4-one (0.5 mmol) in CH$_2$Cl$_2$ (10 mL) was slowly added a 1.0 M solution of BBr$_3$ (2.0 mL, 2 mmol) at 0° C., and the resulting suspension was allowed to warm to room temperature and stirred overnight. After cooling to 0° C., the reaction mixture was quenched with water and concentrated under reduced pressure. The residue was suspended in a mixture of water and EtOAc, and the insoluble product was collected by filtration. The filtrate was extracted with EtOAc twice (2×20 mL), and the combined organic layer was washed with brine, dried over MgSO$_4$, filtered, and concentrated under reduced pressure to give additional product. The combined solid was purified by silica gel column chromatography (eluting with MeOH/CHCl$_3$) and/or directly applied to recrystallization.

7-Hydroxy-3-(4-hydroxyphenyl)-2-[(propen-2-yl)thio]-4H-1-benzopyran-4-one (4a). Using the previous procedure and starting from 3-(4-methoxyphenyl)-7-(phenylmethoxy)-2-[(propen-2-yl)thio]-4H-1-benzopyran-4-one (0.179 g, 0.416 mmol), 0.123 g (91%) of the title compound was obtained as a pale yellow solid: mp 230-232° C. (decomposed); IR (KBr) 3231, 1610, 1561, 1539, 1512, 1497, 1439, 1376, 1245, 1220, 1194, 1174, 1103, 972, 949, 928, 846, 827, 809 cm$^{-1}$; $^1$H NMR (400 MHz, DMSO-d$_6$) δ 10.72 (br s, 1H), 9.50 (br s, 1H), 7.81 (d, J=9.3 Hz, 1H), 6.99 (d, J=8.6 Hz, 2H), 6.85-6.88 (m, 2H), 6.74 (d, J=8.6 Hz, 2H), 5.84 (ddt, J=16.9, 9.9, 6.9Hz, 1H), 5.27 (dd, J=16.9, 1.4 Hz, 1H), 5.09 (dd, J=9.9, 1.4 Hz, 1H), 3.75 (d, J=6.9 Hz, 2H); $^{13}$C NMR (100 MHz, DMSO-d$_6$) δ 173.61, 163.10, 163.07, 158.51, 158.01, 134.75, 132.67, 128.07, 123.49, 122.50, 119.27, 116.24, 115.83, 115.80, 102.70, 34.24; HRMS calculated for $C_{18}H_{14}NaO_4S$ (M+Na)$^+$ 349.0511, found 349.0529. Anal. ($C_{18}H_{14}O_4S.0.1H_2O$) C, H.

7-Hydroxy-3-(4-hydroxyphenyl)-2-[(phenylmethyl)thio]-4H-1-benzopyran-4-one (4b). Using the previous procedure and starting from 3-(4-methoxyphenyl)-7-(phenylmethox))-2-[(phenylmethyl)thio]-4H-1-benzopyran-4-one (0.147 g, 0.305 mmol), 0.106 g (92%) of the title compound was obtained as a white solid: mp 261-264° C. (decomposed); IR (KBr) 3280, 1625, 1605, 1592. 1508, 1459, 1375, 1246, 1228, 1189, 1174, 1111, 966, 948, 843, 821, 694 cm$^{-1}$; $^1$H NMR (400 MHz. DMSO-d$_6$) δ 10.75 (br s, 1H), 9.49 (br s, 1H), 7.79 (d, J=8.7 Hz, 1H), 7.35-7.37 (m, 2H), 7.18-7.29 (m, 0.3H), 6.94 (d, J=8.5 Hz, 2H), 6.91 (d, J=2.2 Hz, 1H), 6.86 (dd, J=8.7, 2.2 Hz, 1H), 6.72 (d, J=8.5 Hz, 2H), 4.36 (s, 2H); $^{13}$C NMR (100 MHz, DMSO-d$_6$) δ 173.51, 163.25, 163.06, 158.48, 158.01. 138.18, 132.61, 129.75, 129.40, 128.20, 128.06, 123.38, 121.96, 116.23, 115.86, 115.81, 102.73, 35.38; HRMS calculated for $C_{22}H_{16}NaO_4S$ (M+Na)$^+$ 399.0667, found 399.0656. Anal. ($C_{22}H_{16}O_4S.0.5H_2O$) C. H.

7-Hydroxy-3-phenyl-2-[(phenylmethyl)thio]-4H-1-benzopyran-4-one (4c). Using the previous procedure and starting from 7-methoxy-3-phenyl-2-[(phenylmethyl)thio]-4H-1-benzopyran-4-one (0.223 g, 0.596 mmol), 0.189 g (88%) of the title compound was obtained as a white solid: mp 215-217° C.; IR (KBr) 3413, 1610, 1559, 1486, 1453, 1375, 1269, 1250, 1219, 1194, 1105, 970. 947, 848, 699 cm$^{-1}$, $^1$H NMR (400 MHz, DMSO-d$_6$) δ 10.80 (br s, 1H), 7.81 (d, J=8.7 Hz, 1H), 7.20-7.37 (m,8H), 7.13-7.19 (m, 2H), 6.94 (d, J=2.2 Hz, 1H), 6.87 (dd, J=8.7, 2.2 Hz, 1H), 4.38 (s, 2H); $^{13}$C NMR (100 MHz, DMSO-d$_6$) δ 173.31, 163.47, 163.20, 158.54, 138.11, 133.26, 131.46, 129.76. 129.41, 128.99, 128 77, 128.24, 128.08, 122.21, 116.20, 115.97, 102.79, 35.39; HRMS calculated for $C_{22}H_{16}NaO_3S$ (M+Na)$^+$ 383.0718, found 383.0710. Anal. ($C_{22}H_{16}O_3S.0.4H_2O$) C, H.

7-Hydroxy-3-phenyl-2-[(4-pyridylmethyl)thio]-4H-1-benzopyran-4-one (4d). Using the previous procedure and starting from 7-methoxy-3-phenyl-2-[(4-pyidylmethyl)thio]-4H-1-benzopyran-4-one (0.165 g, 0.439 mmol), 0.098 g (62%) of the title compound was obtained as a pale yellow solid: mp 229-230° C. (decomposed); IR (KBr) 3427, 1617, 1584, 1544, 1504, 1417, 1366, 1260, 1191, 1102, 1015, 969, 945, 843, 701 cm$^{-1}$; $^1$H NMR (400 MHz, DMSO-d$_6$) δ 10.80 (br s, 1H), 8.48 (d, J=4.0 Hz, 2H), 7.80 (d, J=8.4 Hz, 1H), 7.33-7.40 (m, 5H), 7.16 (d, J=7.0 Hz, 2H), 6.86-6.88 (m, 2H), 4.38 (s, 2H); $^{13}$C NMR (100 MHz, DMSO-d$_6$) δ 173.28, 163.1, 162.72, 158.48, 150.65, 147.82, 133.12, 131.45, 129.06, 128.87, 128.09, 124.61, 122.50, 116.14, 116.01, 102.71, 34.05; HRMS calculated for $C_{21}H_{15}NNaO_3S$ (M+Na)$^+$ 384.0670, found 384.0667. Anal. ($C_{21}H_{15}NO_3S.0.2H_2O$) C, H, N.

7-Hydroxy-3-phenyl-2-[(3-pyridylmethyl)thio]-4H-1-benzopyran-4-one (4e). Using the previous procedure and starting from 7-methoxy-3-phenyl-2-[(3-pyridylmethyl)thio]-4H-1-benzopyran-4-one (0.181 g, 0.482 mmol), 0.082 g (47%) of the title compound was obtained as a yellow solid: mp 194-197° C. (decomposed); IR (KBr) 3053, 1618, 1584, 1542, 1502, 1462, 1366, 1268, 1219, 1187, 1102, 970, 946, 843, 782, 754, 701 cm"; 'H NMR (400 MHz, DMSO-d$_6$) S 10.82 (br s, 1H), 8.73 (br s, 1H), 8.53 (d, J=4.4 Hz, 1H), 8.03 (d, J=7.8 Hz, 1H), 7.81 (d, J=8.7 Hz, 1H), 7.53 (dd, J=7.8, 5.1 Hz, 1H), 7.30-7.39 (m, 3H), 7.13-7.15 (m, 2H), 6.95 (d, J=2.1 Hz, 1H), 6.89 (dd, J=8.7, 2.1 Hz, 1H), 4.46 (s, 2H); $^{13}$C NMR (100 MHz, DMSO-d$_6$) δ 173.51, 163.12, 162.83, 158.55, 148.07, 147.00, 140.30, 136.09, 132.92, 131.36, 129.15, 128.99, 128.13, 125.64, 122.61, 116.10, 116.04, 102.79, 32.23; HRMS calculated for $C_{21}H_{15}NNaO_3S$ (M+Na)$^+$ 384.0670, found 384.0674. Anal. ($C_{21}H_{15}NO_3S.0.3H_2O$) C, H, N.

7-Hydroxy-3-(4-hydroxyphenyl)-2-[(4-pyridylmethyl)thio]-4H-1-benzopyran-4-one (4f). Using the previous procedure and starting from 3-(4-methoxyphenyl)-7-(phenylmethoxy)-2-[(4-pyridylmethyl)thio]-4H-1-benzopyran-4-one (0.173 g, 0.36 mmol), 0.117 g (86%) of the title compound was obtained as a pale yellow solid: mp>240° C. (decomposed); IR (KBr) 3430, 1621, 1607, 1560, 1513, 1499, 1369, 1263, 1234, 1194, 1171, 1107, 950, 807 cm$^{-1}$; $^1$H NMR (400 MHz, DMSO-d$_6$) δ 10.74 (br s, 1H), 9.52 (br s, 1H), 8.76 (d, J=6.4 Hz, 2H), 7.94 (d, J=6.4 Hz, 2H), 7.78 (d, J=9.0 Hz, 1H), 6.97 (d, J=8.5 Hz, 2H), 6.86-6.88 (m, 2H), 6.76 (d, I=8.5 Hz, 2H), 4.58 (s, 2H); $^{13}$C NMR (100 MHz, DMSO-d$_6$) δ 173.49, 163.15, 161.71, 158.42, 158.17, 157.23, 144.66, 132.61, 128.07, 126.94, 123.07, 122.47, 116.14, 115.91, 115.89, 102.83, 34.15; HRMS calculated for $C_{21}H_{15}NNaO_4S$ (M+Na)$^+$ 400.0619, found 400.0627. Anal. ($C_{21}H_{15}NO_4S \cdot 0.1H_2O$) C, H, N.

7-Hydroxy-3-(4-methoxyphenyl)-2-[(4-pyridylmethyl)thiol-411-1-benzopyran-4-one (4g). To a stirred suspension of 3-(4-methoxyphenyl)-7-(phenylmethoxy)-2-[(4-pyridylmethyl)thio]-4H-1-benzopyran-4-one (0.200 g, 0.415 mmol) in Me$_2$S (3.0 mL) and CH$_2$Cl$_2$ (3.0 mL) was slowly added boron trifluoride diethyl etherate (1.52 mL, 12 mmol) at room temperature. The resulting yellow solution was vigorously stilled at room temperature overnight. After cooling to 0° C., the reaction mixture was quenched with water and concentrated under reduced pressure. The residue was suspended in a mixture of water and EtOAc, and the insoluble product was collected by filtration. The filtrate was extracted with EtOAc twice (2×2.5 mL), and the combined organic layer was washed with brine, dried over MgSO$_4$, filtered, and concentrated under reduced pressure to give additional product. The combined solid was purified by silica gel column chromatography (eluting with MeOH/CHCl$_3$) and then recrystallized from ethanol to give a white solid (0.136 g, 84%): mp 197-200° C.; IR (KBr) 3400, 1623, 1606, 1561, 1512, 1455, 1363, 1293, 1247, 1219, 1180, 1106, 1076, 1023, 1003, 968, 856, 822 cm$^{-1}$; $^1$H NMR (400 MHz, DMSO-d$_6$) δ 10.76 (br s, 1H), 8.79 (d, J=6.4 Hz, 2H), 8.01 (d, J=6.5 Hz, 2H), 7.80 (d, J=8.5 Hz, 1H), 7.11 (d, J=8.7 Hz, 2H), 6.94 (d, J=8.7 Hz, 2H), 6.86-6.89 (m, 2H), 4.56 (s, 2H), 3.73 (s, 3H); $^{13}$C NMR (100 MHz, DMSO-d$_6$) δ 173.45, 163.22, 161.74, 159.96, 158.48, 158.09, 144.07, 132.68, 128.10, 127.18, 124.80, 122 28, 116.13, 115.98, 114.57, 102.87, 56.00, 34.12; HRMS calculated for $C_{22}H_{18}NO_4S$ (M+H)$^+$ 392.0956, found 392.0962. Anal. ($C_{22}H_{17}NOS \cdot 0.1H_2O$) C, H, N.

Preparation of human placental microsomes. Human term placentas were processed immediately after delivery from The Ohio State University Hospitals at 4° C. The placenta was washed with normal saline and connective and vascular tissue was removed. Microsomes were prepared from the remaining tissue using the method described by Kellis and Vickery. Microsomel suspensions were stored at −80° C. until required.

Inhibition Study. Inhibition of human placental aromatase was determined by monitoring the amount of H$_2$O released as the enzyme converts [Iβ-$^3$H]androst-4-ene-3,17-dione to estrone. Aromatase activity assays were carried in 0.1 M potassium phosphate buffer (pH 7.0) with 5% propylene glycol. All samples contained a NADPH regenerating system consisting of 2.85 mM glucose-6-phosphate, 1.8 mM NADP' and 1.5 units of glucose-6-phosphate dehydrogenase (Sigma, St. Louis, Mo.). Samples contained 100 nM androst-4-ene-3,17-dione (400,000-450,000 dpm). Reactions were initiated with the addition of 50 µg microsomal protein. Incubations were allowed to proceed for 15 minutes in a shaking water bath at 37° C. Reactions were quenched by the addition of 2.0 mL of chloroform. Samples were then vortexed and centrifuged for 5 minutes and the aqueous layer was removed. The aqueous layer was subsequently extracted twice in the same manner with 2.0 mL chloroform. A 0.5 mL aliquot of the final aqueous layer was combined with 5 mL 3a70B scintillation cocktail (Research Products International Corp., Mt. Prospect, Ill.) and the amount of radioactivity determined. Each sample was run in triplicate and background values were determined with microsomal protein inactivated by boiling. Samples containing 50 µM (±) aminoglutethimide (Sigma, St. Louis, Mo.) were used a positive control. IC$_{50}$ signioidal dose-response data were analyzed with the Graphpad Prism (Version 3.0) program.

Kinetic study. Enzyme kinetic studies of compounds 3j, 4f, and 4g were conducted to investigate the nature of aromatase inhibition. Michaelis-Menten enzyme kinetic parameters were determined by varying the concentration of androst-4-ene-3,17-dione from 10 to 300 nM in the prescence of a fixed concentration of 0, 100, 500, and 2000 nM inhibitor. Assay conditions were the same as those described in the IC$_{50}$ studies except reactions were initiated by the addition of 15 lag microsomal protein. Analysis of the enzyme kinetic data was performed with the weighted linear regression analysis previously described by Cleland.

All documents referenced herein are incorporated by reference.

Although this invention has been described with respect to specific embodiments, the details of these embodiments are not to be construed as limitations.

The invention claimed is:

1. A compound of formula I:

wherein X is selected from the group consisting of O, N, S, SO, SO$_2$, and S(CH$_2$)$_n$, wherein n=1-10;

R$_1$ and R$_2$ can be the same or different and are selected from the group consisting of H, OH, OCH$_3$, OCH$_2$CH$_3$, OCH$_2$C$_6$H$_5$, NH$_2$, NHCH$_3$, N(CH$_3$)$_2$, CH$_3$, CH$_2$CH$_3$, CH$_2$CH$_2$CH$_3$, CH(CH$_3$)$_2$, C(CH$_3$)$_3$, NO$_2$, F, Cl, Br, CF$_3$, SH, SCH$_3$, SCH$_2$CH$_3$, OCOCH$_3$, OCOC(CH$_3$)$_3$, OCOCH$_2$COOH, and CN; and R$_3$ comprises a nitrogen-containing heterocyclic ring; or a salt, ester, derivative, or prodrug thereof.

2. The compound of claim 1 wherein X is selected from the group consisting of S or S(CH$_2$)$_n$, wherein n=1, 2, or 3.

3. The compound of claim 1 wherein the heterocyclic ring, R$_3$ comprises a 5- or 6-membered ring; and wherein the ring comprises from 1-3 nitrogen atoms in the ring.

4. The compound of claim 3 wherein the heterocyclic ring is selected from the group consisting of imidazole, triazole, pyrimidine, and pyridine.

5. The compound of claim 1 further comprising one or more substituents on the heterocyclic ring.

6. The compound of claim 5 wherein the substituents are selected from the group consisting of H, OH, OCH$_3$, OCH$_2$CH$_3$, NH$_2$, NHCH$_3$, N(CH$_3$)$_2$, NO$_2$, CH$_3$, CH$_2$CH$_3$, CH$_2$CH$_2$CH$_3$, CH(CH$_3$)$_2$, C(CH$_3$)$_3$, F, Cl, Br, CF$_3$, SH, SCH$_3$, SCH$_2$CH$_3$, CN and combinations thereof.

7. The compound of claim 1 wherein X—R$_3$ is selected from the group consisting of:

wherein n is 0-3 and R$_4$ is selected from the group consisting of H, OH, OCH$_3$, OCH$_2$CH$_3$, NH$_2$, NHCH$_3$, N(CH$_3$)$_2$, NO$_2$, CH$_3$, CH$_2$CH$_3$, CH$_2$CH$_2$CH$_3$, CH(CH$_3$)$_2$, C(CH$_3$)$_3$, F, Cl, Br, CF$_3$, SH, SCH$_3$, SCH$_2$CH$_3$, CN and combinations thereof.

8. The compound of claim 1 wherein R$_1$ is H, R$_2$ is OCH$_2$C$_6$H$_5$, and R$_3$ is (4-pyridyl)methyl;

or a salt, ester, derivative or prodrug thereof.

9. The compound of claim 1 wherein R$_1$ is OH, R$_2$ is OH, and R$_3$ is (4-pyridyl)methyl;

or a salt, ester, derivative or prodrug thereof.

10. The compound of claim 1 wherein R$_1$ is OCH$_3$, R$_2$ is OH, and R$_3$ is (4-pyridyl)methyl;

or a salt, ester, derivative or prodrug thereof.

* * * * *

UNITED STATES PATENT AND TRADEMARK OFFICE
CERTIFICATE OF CORRECTION

| | | |
|---|---|---|
| PATENT NO. | : 7,572,919 B2 | Page 1 of 1 |
| APPLICATION NO. | : 11/212229 | |
| DATED | : August 11, 2009 | |
| INVENTOR(S) | : Brueggemeier et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 404 days.

Signed and Sealed this

Seventh Day of September, 2010

David J. Kappos
*Director of the United States Patent and Trademark Office*